US00PP17516P2

(12) United States Plant Patent
Leue

(10) Patent No.: US PP17,516 P2
(45) Date of Patent: Mar. 20, 2007

(54) ***ANGELONIA* PLANT NAMED 'BALANGDARLA'**

(50) Latin Name: *Angelonia angustifolia*
Varietal Denomination: Balangdarla

(75) Inventor: Ellen Leue, DeKalb, IL (US)

(73) Assignee: Ball Horticultural Company, West Chicago, IL (US)

( * ) Notice: Subject to any disclaimer, the term of this patent is extended or adjusted under 35 U.S.C. 154(b) by 82 days.

(21) Appl. No.: 11/270,069

(22) Filed: Nov. 9, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

European Plant Breeders' Rights application No. 2005/2328 filed Nov. 16, 2005.

*Primary Examiner*—Kent Bell
*Assistant Examiner*—Louanne Krawczewicz Myers
(74) *Attorney, Agent, or Firm*—Audrey Charles

(57) ABSTRACT

A new and distinct cultivar of *Angelonia* plant named 'Balangdarla' characterized by its medium lavender-colored flowers, good basal branching, and moderately vigorous, upright growth habit.

1 Drawing Sheet

Latin name of genus and species of plant claimed: *Angelonia angustifolia.*
Variety denomination: 'Balangdarla'.

BACKGROUND OF THE INVENTION

The present invention relates to a new and distinct cultivar of *Angelonia* plant botanically known as *Angelonia angustifolia* and hereinafter referred to by the cultivar name 'Balangdarla'.

The new cultivar was developed by the inventor in a controlled breeding program during November 2002 at Elburn, Ill. The objective of the breeding program was the development of *Angelonia* cultivars with continuous flowering, good branching, and moderately vigorous growth habit.

The female (seed) parent of the new cultivar was the proprietary *Angelonia angustifolia* breeding selection designated 105-1-1,2-2-1, not patented, characterized by its white-colored flowers, medium vigor, and upright growth habit. The male (pollen) parent of the new cultivar was the proprietary *Angelonia angustifolia* breeding selection designated 156-2-2, not patented, characterized by its deep violet blue-colored flowers, medium vigor, and upright growth habit. The new cultivar was discovered and selected by the inventor as a single flowering plant within the progeny of the above stated cross-pollination during June 2003 in a controlled environment at Elburn, Ill.

Asexual reproduction of the new cultivar by terminal stem cuttings since June 2003 at West Chicago, Ill. has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balangdarla' as a new and distinct cultivar of *Angelonia* plant:

1. Medium lavender-colored flowers;
2. Good basal branching; and
3. Moderately vigorous, upright growth habit.

Plants of the new cultivar differ from plants of the female parent primarily in flower color and from plants of the male parent primarily in flower color.

Of the *Angelonia* cultivars known to the inventor, the most similar to 'Balangdarla' is the *Angelonia* cultivar Balangbeke, U.S. Plant Pat. No. 15,546. However, in side-by-side comparisons, plants of the new cultivar differ from plants of 'Balangbeke' in the following characteristics:

1. Plants of the new cultivar have a taller growth habit compared to 'Balangbeke'; and
2. Plants of the new cultivar have a narrower plant diameter compared to 'Balangbeke'.

Of the *Angelonia* cultivars known to the inventor, another cultivar similar to 'Balangdarla' is the *Angelonia* cultivar Balangimla, U.S. Plant Pat. No. 13,922. However, in side-by-side comparisons, plants of the new cultivar differ from plants of 'Balangimla' in the following characteristics:

1. Plants of the new cultivar have a different flower color compared to 'Balangimla';
2. Plants of the new cultivar have larger flowers as measured by flower length compared to 'Balangimla'; and
3. Plants of the new cultivar have shorter racemes compared to 'Balangimla'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balangdarla'. The plants were grown in 10 cm pots for 11 weeks in a greenhouse at West Chicago, Ill.

DETAILED BOTANICAL DESCRIPTION

Figure 1:
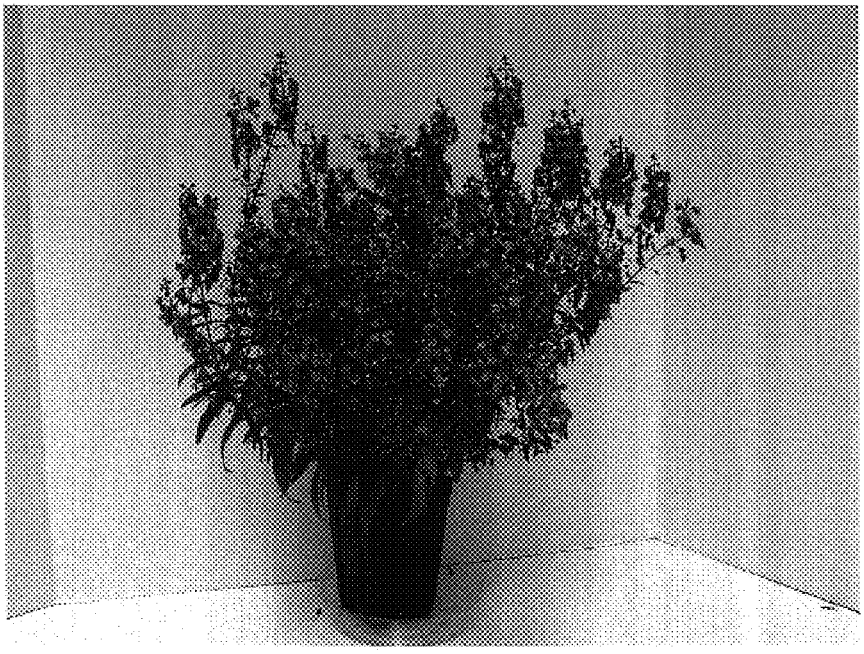
FIG. 1 illustrates a side view of the overall growth and flowering habit of 'Balangdarla'.
Figure 2:
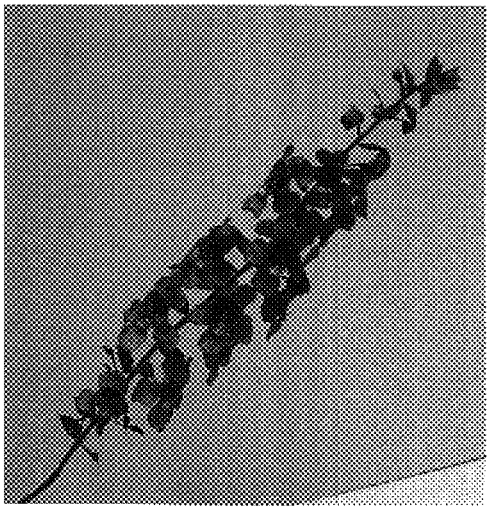
FIG. 2 illustrates a close-up view of the inflorescence of 'Balangdarla'.
Figure 3:
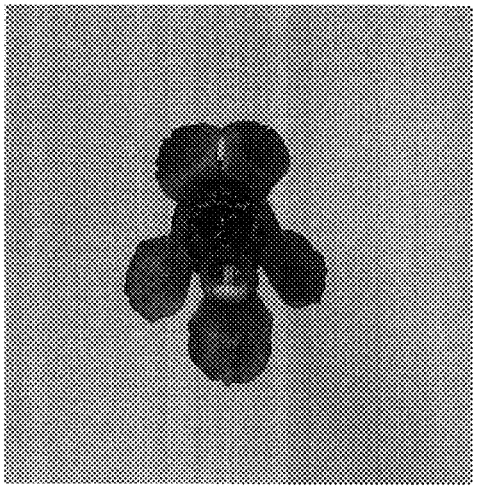
FIG. 3 illustrates a close-up view of an individual flower of 'Balangdarla'.

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where color terms of ordinary significance are used. The color values were determined on Apr. 13, 2005. The readings were taken between 1:00 p.m. and 3:00 p.m. under natural light conditions.

The following descriptions and measurements describe plants produced from cuttings taken from stock plants and grown in a double polycarbonate-covered greenhouse under conditions comparable to those used in commercial practice. The plants were grown in 10 cm pots for 11 weeks while utilizing a soilless growth medium. Greenhouse temperatures were maintained at approximately 75° F. to 85° F. (24° C. to 29° C.) during the day and approximately 62° F. to 70° F. (17° C. to 21° C.) during the night. Greenhouse light levels were maintained at approximately 6,000 to 10,000 footcandles during the day.

Botanical classification: *Angelonia angustifolia,* cultivar Balangdarla.

Parentage:

*Female (seed) parent.*—Proprietary *Angelonia angustifolia* breeding selection designated 105-1-1,2-2-2-1, not patented.

*Male (pollen) parent.*—Proprietary *Angelonia angustifolia* breeding selection 156-2-2, not patented.

Propagation:

*Type cutting.*—Terminal stem.

*Time to initiate roots.*—Approximately 7 to 9 days.

*Time to develop roots.*—Approximately 21 to 28 days.

*Root description.*—Fine and Fibrous.

*Rooting habit.*—Freely branching.

Plant description:

*Crop time.*—Approximately 6 to 7 weeks from a rooted cutting.

*Habit of growth.*—Moderately vigorous.

*Form.*—Upright.

*Size.*—Height (from soil level to top of plant plane): Approximately 25.6 cm. Diameter (area of spread): Approximately 34.7 cm.

*Main branch.*—Quantity per plant: Approximately 4. Shape: Square in cross section. Strength: Somewhat brittle. Length from soil level to base of raceme: Approximately 32.6 cm. Diameter: Approximately 3.1 mm. Texture: Glabrous. Color: 144A. Internode length at center of branch: Approximately 2.4 cm.

*Foliage.*—Quantity of leaves per main branch: Approximately 20. Type: Simple. Fragrance: None. Arrangement: Opposite. Orientation to stem: Perpendicular or obtuse. Shape: Elliptic. Margin: Widely dentate. Apex: Acute. Base: Sessile. Length of leaf at center of branch: Approximately 6.3 cm. Width of leaf at center of branch: Approximately 1.3 cm. Texture of upper and lower surfaces: Glabrous. Venation pattern: Pinnate. Color of upper surface of young and mature foliage: Darker than 139A with venation of 144C. Color of lower surface of young and mature foliage: 138A with venation of 144C.

Flowering description:

*Flowering habit.*—'Balangdarla' is freely flowering under outdoor growing conditions with substantially continuous blooming from spring through autumn and year round in greenhouse environment.

*Time to first flower.*—Approximately 11 weeks from sticking of unrooted cutting.

*Lastingness of individual bloom on the plant.*—Approximately 7 to 10 days.

*Inflorescence type/sescription.*—Terminal racemes. Length: Approximately 12.7 cm. Width: Approximately 4.2 cm. Number per plant: Approximately 6 open racemes per plant. Number of fully open flowers per raceme at any one time: Approximately 14.

Flower description:

*Type/fragrance.*—Bilabiate. Very slight, sweet fragrance.

*Bud.*—Rate of opening: 3 to 4 days from first color to fully open. Shape: Globular. Length: Approximately 7.4 mm. Diameter: Approximately 5.4 mm. Color of upper surface: N87C. Color of lower surface: N77D with spots of N77A.

*Flower size/aspect.*—Length: Approximately 2.3 cm. Width: Approximately 2.0 cm. Depth: Approximately 8.7 mm. Aspect: Facing outward.

*Petals.*—Quantity: 5 per flower, fused at base forming a throat, an upper lip with two petals, and a lower lip with three petals — one central petal and one lateral petal on each side. Petal shape of upper lip and lower lip petals: Obovate.

*Upper lip.*—Petal apex: Obtuse. Petal margin: Entire. Length of petals from throat: Approximately 6.6 mm. Width of each petal: Approximately 7.4 mm. Color of upper surface: Between N82A and N87A. Color of lower surface: N82B. Texture of upper surface: Densely glandular-pubescent. Texture of lower surface: Glabrous.

*Lower lip, lateral petals.*—Petal apex: Obtuse. Petal margin: Entire. Length of petals from throat: Approximately 8.4 mm. Width of each petal: Approximately 8.5 mm. Color of upper surface: Closest to but darker than N82A. Color of lower surface: N82B. Texture of upper and lower surfaces: Glandular-pubescent.

*Lower lip, central petal.*—Petal apex: Obtuse. Petal margin: Entire. Length of petal from palate: Approximately 6.9 mm. Width of petal: Approximately 7.4 mm. Color of upper surface: N87D with N82A along margin. Color of lower surface: N87B. Texture of upper surface of central petal: Glabrous, with dense pubescence along margin. Texture of lower surface of central petal: Glandular-pubescent. Gland color: Colorless, translucent.

*Throat.*—Length: Approximately 5.8 mm. Width: Approximately 5.3 mm. Texture of inner and outer surfaces: Glabrous. Color of inner and outer surfaces: 76C with spots of N79A. Palate color: 155D with spots at edges of 83A. Palate texture: Glabrous. Teeth color: 145C.

*Pedicel.*—Strength: Good. Length: Approximately 1.1 cm. Diameter: Approximately 0.4 mm. Angle to stem: Acute. Texture: Glabrous. Color: 144A with overlay of 186C.

*Calyx.*—Shape: Five-pointed star, cupped. Width: Approximately 5.0 mm.

*Sepals.*—Quantity per flower: 5. Shape: Lanceolate. Margin: Entire. Base: Fused. Apex: Acuminate. Length: Approximately 3.0 mm. Width: Approximately 1.7 mm. Texture of upper and lower surfaces: Glabrous. Color of upper and lower surfaces: 144A with overlay of 186C.

*Reproductive organs.*—Androecium: Stamen quantity: 4 per flower. Stamen length: Approximately 4.0 mm. Filament color: 91C. Anther shape: Bilobed. Anther length: Approximately 0.8 mm. Anther color: 93A. Amount of pollen: Abundant. Pollen color: 92D. Gynoecium: Pistil quantity: 1 per flower. Pistil length: Approximately 3.5 mm. Stigma length: Approximately 0.3 mm. Stigma color: 91C. Style length: Approximately 2.0 mm. Style color: Lighter than 155A. Ovary diameter: Approximately 1.2 mm. Ovary texture: Glabrous. Ovary color: 144C with streaks of 83A.

Seed and fruit production. Neither seed nor fruit production has been observed.

Disease and pest resistance: Resistance to pathogens and pests common to *Angelonia* has not been observed.

What is claimed:

1. A new and distinct cultivar of *Angelonia* plant named 'Balangdarla', substantially as herein shown and described.

* * * * *